(12) United States Patent
Dorn et al.

(10) Patent No.: US 8,292,950 B2
(45) Date of Patent: Oct. 23, 2012

(54) STENT WITH RADIOPAQUE MARKER

(75) Inventors: Juergen Dorn, Neulussheim (DE); Thilo Wack, Durmersheim (DE)

(73) Assignee: C. R. Bard, Inc., Murray Hill, NJ (US)

( * ) Notice: Subject to any disclaimer, the term of this patent is extended or adjusted under 35 U.S.C. 154(b) by 456 days.

(21) Appl. No.: 12/528,289

(22) PCT Filed: Feb. 21, 2008

(86) PCT No.: PCT/EP2008/052121
§ 371 (c)(1),
(2), (4) Date: Aug. 26, 2009

(87) PCT Pub. No.: WO2008/101987
PCT Pub. Date: Aug. 28, 2008

(65) Prior Publication Data
US 2010/0114298 A1    May 6, 2010

(30) Foreign Application Priority Data

Feb. 21, 2007 (GB) .................................. 0703379.8

(51) Int. Cl.
*A61F 2/06* (2006.01)
(52) U.S. Cl. ...................................................... 623/1.35
(58) Field of Classification Search ................ 623/1.34, 623/1.22, 1.13, 1.15, 1.36
See application file for complete search history.

(56) References Cited

U.S. PATENT DOCUMENTS

| | | | | |
|---|---|---|---|---|
| 5,464,419 A | * | 11/1995 | Glastra | 606/194 |
| 5,527,353 A | * | 6/1996 | Schmitt | 623/1.44 |
| 5,591,223 A | * | 1/1997 | Lock et al. | 623/1.17 |
| 5,645,532 A | * | 7/1997 | Horgan | 604/117 |
| 5,725,572 A | * | 3/1998 | Lam et al. | 623/1.16 |
| 5,741,327 A | * | 4/1998 | Frantzen | 623/1.34 |
| 5,759,192 A | | 6/1998 | Saunders | |
| 5,800,511 A | * | 9/1998 | Mayer | 623/1.34 |
| 5,824,042 A | * | 10/1998 | Lombardi et al. | 623/1.13 |
| 5,824,077 A | * | 10/1998 | Mayer | 623/11.11 |

(Continued)

FOREIGN PATENT DOCUMENTS

DE  04130431 A1  3/1993

(Continued)

OTHER PUBLICATIONS

U.S. Appl. No. 10/362,040, filed Jun. 27, 2003 Notice of Allowance dated Jun. 22, 2011.

(Continued)

*Primary Examiner* — Alvin J. Stewart
(74) *Attorney, Agent, or Firm* — Rutan & Tucker, LLP

(57) ABSTRACT

The invention concerns a method of providing a stent with a radiopaque marker comprising the steps of: i) providing in the stent a radiopaque marker carrier portion; ii) sleeving the carrier portion with radiopaque material, with an insulating surface between the carrier and the marker material, and iii) plastically deforming material within the sleeve of radiopaque material, to secure the sleeve on the carrier portion. The invention further concerns a stent with a radiopaque marker, the stent exhibiting a generally annular form with luminal and abluminal major surfaces, the marker also exhibiting opposed major luminal and abluminal surfaces characterized in that i) the marker envelops a carrier portion of the stent and is electrically insulated from it; ii) portions of the material of the marker which exhibit evidence of plastic deformation secure the marker on the carrier portion.

14 Claims, 3 Drawing Sheets

U.S. PATENT DOCUMENTS

| | | | | |
|---|---|---|---|---|
| 5,843,118 | A * | 12/1998 | Sepetka et al. | 623/1.15 |
| 5,858,556 | A * | 1/1999 | Eckert et al. | 428/586 |
| 5,861,027 | A * | 1/1999 | Trapp | 623/1.15 |
| 5,868,783 | A | 2/1999 | Tower | |
| 6,022,374 | A | 2/2000 | Imran | |
| 6,056,187 | A | 5/2000 | Acciai et al. | |
| 6,086,611 | A * | 7/2000 | Duffy et al. | 623/1.35 |
| 6,099,561 | A * | 8/2000 | Alt | 623/1.44 |
| 6,174,329 | B1 * | 1/2001 | Callol et al. | 623/1.34 |
| 6,293,966 | B1 | 9/2001 | Frantzen | |
| 6,334,871 | B1 * | 1/2002 | Dor et al. | 623/1.34 |
| 6,379,381 | B1 | 4/2002 | Hossainy et al. | |
| 6,387,123 | B1 * | 5/2002 | Jacobs et al. | 623/1.34 |
| 6,409,752 | B1 * | 6/2002 | Boatman et al. | 623/1.15 |
| 6,451,047 | B2 * | 9/2002 | McCrea et al. | 623/1.13 |
| 6,471,721 | B1 * | 10/2002 | Dang | 623/1.34 |
| 6,540,777 | B2 | 4/2003 | Stenzel et al. | |
| 6,585,757 | B1 * | 7/2003 | Callol | 623/1.16 |
| 6,676,700 | B1 * | 1/2004 | Jacobs et al. | 623/1.34 |
| 6,797,217 | B2 * | 9/2004 | McCrea et al. | 264/229 |
| 7,060,093 | B2 * | 6/2006 | Dang et al. | 623/1.42 |
| 7,135,038 | B1 * | 11/2006 | Limon | 623/1.15 |
| 7,175,654 | B2 * | 2/2007 | Bonsignore et al. | 623/1.15 |
| 7,462,190 | B2 * | 12/2008 | Lombardi | 623/1.13 |
| 7,468,071 | B2 * | 12/2008 | Edwin et al. | 623/1.13 |
| 7,479,157 | B2 * | 1/2009 | Weber et al. | 623/1.15 |
| 7,691,461 | B1 * | 4/2010 | Prabhu | 428/36.9 |
| 8,043,364 | B2 * | 10/2011 | Lombardi et al. | 623/1.34 |
| 2002/0193867 | A1 * | 12/2002 | Gladdish et al. | 623/1.15 |
| 2002/0193869 | A1 * | 12/2002 | Dang | 623/1.15 |
| 2003/0135254 | A1 * | 7/2003 | Curcio et al. | 623/1.1 |
| 2003/0144725 | A1 * | 7/2003 | Lombardi | 623/1.13 |
| 2003/0216807 | A1 * | 11/2003 | Jones et al. | 623/1.22 |
| 2004/0015228 | A1 * | 1/2004 | Lombardi et al. | 623/1.18 |
| 2004/0015229 | A1 * | 1/2004 | Fulkerson et al. | 623/1.22 |
| 2004/0073291 | A1 | 4/2004 | Brown et al. | |
| 2004/0236400 | A1 * | 11/2004 | Edwin et al. | 623/1.12 |
| 2004/0236409 | A1 * | 11/2004 | Pelton et al. | 623/1.18 |
| 2004/0254637 | A1 * | 12/2004 | Yang et al. | 623/1.34 |
| 2005/0049682 | A1 | 3/2005 | Leanna et al. | |
| 2005/0060025 | A1 * | 3/2005 | Mackiewicz et al. | 623/1.34 |
| 2005/0172471 | A1 | 8/2005 | Vietmeier | |
| 2006/0216431 | A1 | 9/2006 | Kerrigan | |
| 2006/0265049 | A1 * | 11/2006 | Gray et al. | 623/1.16 |
| 2007/0219624 | A1 * | 9/2007 | Brown et al. | 623/1.15 |
| 2008/0051885 | A1 * | 2/2008 | Llanos et al. | 623/1.42 |
| 2008/0188924 | A1 * | 8/2008 | Prabhu | 623/1.16 |
| 2009/0125092 | A1 * | 5/2009 | McCrea et al. | 623/1.11 |
| 2009/0125099 | A1 * | 5/2009 | Weber et al. | 623/1.34 |
| 2009/0200360 | A1 * | 8/2009 | Wack | 228/171 |
| 2009/0204203 | A1 * | 8/2009 | Allen et al. | 623/1.34 |
| 2010/0070021 | A1 | 3/2010 | Wack et al. | |
| 2010/0211161 | A1 * | 8/2010 | Dreher | 623/1.16 |
| 2011/0196473 | A1 * | 8/2011 | McCrea et al. | 623/1.12 |
| 2011/0198327 | A1 * | 8/2011 | Prabhu | 219/121.72 |
| 2011/0245905 | A1 * | 10/2011 | Weber et al. | 623/1.15 |
| 2011/0319977 | A1 * | 12/2011 | Pandelidis et al. | 623/1.15 |

FOREIGN PATENT DOCUMENTS

| | | |
|---|---|---|
| DE | 29621207 U1 | 1/1997 |
| DE | 19728337 A1 | 1/1999 |
| DE | 29904817 U1 | 5/1999 |
| DE | 10201151 A1 | 7/2003 |
| EP | 0709068 A2 | 5/1996 |
| EP | 0800800 A1 | 10/1997 |
| EP | 0847733 A1 | 6/1998 |
| EP | 1157673 A2 | 11/2001 |
| EP | 1212991 A2 | 6/2002 |
| EP | 1255507 A1 | 11/2002 |
| EP | 1356789 A1 | 10/2003 |
| EP | 1488763 A2 | 12/2004 |
| FR | 2626046 A1 | 7/1989 |
| WO | 9503010 A1 | 2/1995 |
| WO | 9733534 A1 | 9/1997 |
| WO | 9915108 A1 | 1/1999 |
| WO | 0064375 A1 | 11/2000 |
| WO | 0158384 A1 | 8/2001 |
| WO | 0215820 A2 | 2/2002 |
| WO | 03101343 A1 | 12/2003 |
| WO | WO-2004058384 A1 | 7/2004 |
| WO | 2005072652 A1 | 8/2005 |
| WO | 2008006830 A1 | 1/2008 |
| WO | 2008022950 A1 | 2/2008 |
| WO | 2008068279 A1 | 6/2008 |
| WO | WO-2008101987 A1 | 8/2008 |

OTHER PUBLICATIONS

U.S. Appl. No. 12/373,116, filed Jul. 14, 2009 Advisory Action dated Jul. 26, 2011.

U.S. Appl. No. 12/373,116, filed Jul. 14, 2009 Final Office Action dated Apr. 27, 2011.

U.S. Appl. No. 12/438,330, filed Feb. 20, 2009 Office Action dated Mar. 4, 2011.

U.S. Appl. No. 12/517,096, filed Jun. 1, 2009 Office Action dated May 6, 2011.

U.S. Appl. No. 10/362,040, filed Jun. 27, 2003 Final Office Action dated Aug. 30, 2010.

U.S. Appl. No. 12/438,330, filed Feb. 20, 2009 Advisory Action dated Oct. 14, 2010.

U.S. Appl. No. 12/438,330, filed Feb. 20, 2009 Office Action dated Aug. 5, 2010.

May 9, 2008 International Search Report in international application No. PCT/EP2008/052121 filed on Feb. 21, 2008.

May 9, 2008 Written Opinion of the ISA in international application No. PCT/EP2008/052121 filed on Feb. 21, 2008.

Aug. 26, 2009 International Preliminary Report on Patentability in international application No. PCT/EP2008/052121 filed on Feb. 21, 2008.

Database Wikipedia, Sep. 11, 2007, "Lumen (anatomy)" XP 002453737 abstract.

International Application No. PCT/EP2001/009467 International Preliminary Examination Report Sep. 17, 2002.

International Application No. PCT/EP2001/009467 International Search Report dated Feb. 18, 2002.

International Application No. PCT/EP2007/057041 filed Jul. 10, 2007 International Preliminary Report on Patentability dated Jan. 13, 2009.

International Application No. PCT/EP2007/057041 filed Jul. 10, 2007 International Search Report dated Oct. 18, 2007.

International Application No. PCT/EP2007/057041 filed Jul. 10, 2007 Written Opinion Jan. 10, 2009.

International Application No. PCT/EP2007/058416 filed Aug. 14, 2007 International Preliminary Report on Patentability dated Feb. 24, 2009.

International Application No. PCT/EP2007/058416 filed Aug. 14, 2007 International Search Report dated Nov. 22, 2007.

International Application No. PCT/EP2007/058416 filed Aug. 14, 2007 Written Opinion dated Feb. 23, 2009.

International Application No. PCT/EP2007/063347 filed Dec. 5, 2007 International Search Report dated Jun. 10, 2009.

International Application No. PCT/EP2007/063347 filed Dec. 5, 2007 Written Opinion dated Jun. 10, 2009.

International Application No. PCT/EP2007/063347 filed on Dec. 5, 2007 International Search Report dated Feb. 4, 2008.

U.S. Appl. No. 10/362,040, filed Jun. 27, 2003 Advisory Action dated Jan. 9, 2009.

U.S. Appl. No. 10/362,040, filed Jun. 27, 2003 Advisory Action dated Nov. 29, 2006.

U.S. Appl. No. 10/362,040, filed Jun. 27, 2003 Office Action dated Aug. 18, 2008.

U.S. Appl. No. 10/362,040, filed Jun. 27, 2003 Office Action dated Aug. 2, 2006.

U.S. Appl. No. 10/362,040, filed Jun. 27, 2003 Office Action dated Dec. 10, 2007.

U.S. Appl. No. 10/362,040, filed Jun. 27, 2003 Office Action dated Feb. 23, 2010.

U.S. Appl. No. 10/362,040, filed Jun. 27, 2003 Office Action dated Jan. 10, 2006.

U.S. Appl. No. 10/362,040, filed Jun. 27, 2003 Office Action dated Jul. 15, 2009.
U.S. Appl. No. 10/362,040, filed Jun. 27, 2003 Office Action dated Jun. 23, 2005.
U.S. Appl. No. 10/362,040, filed Jun. 27, 2003 Office Action dated Jun. 5, 2007.
U.S. Appl. No. 12/438,330, filed Feb. 20, 2009 Office Action dated Mar. 16, 2010.
EP 07802603.6 filed Aug. 14, 2007 Office Action dated Dec. 13, 2010.
U.S. Appl. No. 10/362,040, filed Jun. 27, 2003 Advisory Action dated Dec. 16, 2010.
U.S. Appl. No. 12/373,116, filed Jul. 14, 2009 Non-Final Office Action dated Nov. 10, 2010.

* cited by examiner

STENT WITH RADIOPAQUE MARKER

PRIORITY

This application is a U.S. national stage application under 35 USC §371 of International Application No PCT/EP2008/052121, filed Feb. 21, 2008, claiming the benefit of priority to United Kingdom Patent Application No. GB 0703379.8, filed Feb. 21, 2007, each of which is incorporated by reference in its entirety into this application.

TECHNICAL FIELD

This invention relates to a stent with a radiopaque marker, and a method for making such a stent. The stent is generally annular, with luminal and abluminal major surfaces, and the marker also exhibits opposed major luminal and abluminal surfaces. One example of such a stent and marker is shown in WO2002/015820 of the present applicant. Another is EP-A-1488763, which discloses the features of the pre-characterizing parts of the independent claims below.

BACKGROUND OF THE INVENTION

For accurate placement of stents at a target location within the body of the patient, it is customary to use radiological techniques, for which the stent must be such that it can be imaged. The biologically compatible materials from which stents are usually made (stainless steel and nickel-titanium shape memory alloy) are not as opaque to x-rays as one would wish, for the purpose of radiologically tracking their progress through the body to the precise location for deployment, so it is often useful to equip such stents with one or more radiopaque markers of a biologically compatible material that is more opaque, to the medical x-rays used by the radiologist, than the material of the stent as such. Noble metals such as gold or silver, platinum or palladium can be used, but tantalum is particularly attractive for use with nickel-titanium stents because it is of similar electrochemical potential thereby reducing to acceptable levels the rates of electrochemical corrosion that follow from galvanic battery action within the electrolyte provided by the bodily fluid in the lumen in which the stent is located.

In above mentioned WO2002/015820 welding techniques are used to ensure that markers cannot separate from a nickel-titanium stent, after deployment of the stent. Thus, the marker is in full electrically-conductive contact with the metal of the stent. Breaking that full electrical contact would be useful, to reduce the rate of galvanic dissolution of metal after deployment of the stent, but a way would need to be found, to join together the marker and the stent securely enough to eliminate the risk of separation after deployment, in substitution for the currently used joining method, welding. The present invention takes up this challenge, and offers a solution.

SUMMARY OF THE INVENTION

In accordance with a first aspect of the invention, there is provided a method of providing a stent with a radiopaque marker, the method, as defined in claim 1 below, including the steps of:
i) providing in the stent a radiopaque marker carrier portion
ii) sleeving the carrier portion with radiopaque material with an insulating surface between the carrier and the marker material, and
iii) plastically deforming material within the sleeve of radiopaque material, to secure the sleeve on the carrier portion.

In accordance with a second aspect of the invention, there is provided a stent with a radiopaque marker, as defined in claim 1 below, the stent exhibiting a generally annular form with luminal and abluminal major surfaces, the marker also exhibiting opposed major luminal and abluminal surfaces, wherein i) the marker envelops a carrier portion of the stent and is electrically insulated from it and ii) portions of the material of the marker which exhibit evidence of plastic deformation secure the marker on the carrier portion.

For maximum radiological visibility of a stent, the entire mass of material forming the stent would be of radiopaque material. When that is not feasible, an architecture almost as useful to those wanting to know where the stent is within the human body would be a stent cylinder that has at each end a complete ring of radiopaque material. If one knows with precision where are the ends of the stent, one knows with certainty where is the remainder of the length of the stent, namely, in between the two end markers.

One attraction of the marker architecture taught in the above mentioned WO2002/015820 is that it presents during the transluminal delivery of the stent, an architecture in which there is a more or less unbroken ring of radiopaque material at each end of the stent cylinder that is provided by a "ring of spoons". The radiopaque material of the spoons can be the full wall thickness of the stent matrix (or even thicker), which is particularly advantageous for radiological visibility.

With the sleeving concept of the present invention, there is a "sandwich" in which the filling is provided by stent material rather than radiopaque marker material. If the thickness of the sandwich filling is no different from the remainder of the stent structure, then the radiopaque marker zones are going to have a radial thickness which is greater than the thickness of the stent annulus everywhere else, by double the thickness of the radiopaque material wrapped around the carrier portion in the marker zone. However, since the carrier portion need not be making any contribution to the stenting force on bodily tissue radially outside the stenting annulus, the wall thickness of the carrier portion, in the radial direction, could be significantly less than the wall thickness of the stent elsewhere, thereby opening up the possibility for significant radial thicknesses of radiopaque material without unacceptable thickening of the wall of the stent annulus, locally, in the marker zones of the stent.

In above mentioned WO2002/015820 each radiopaque marker spoon is cantilevered out from the end of the stent matrix on a spigot portion of stenting metal that protrudes from the end of the stenting ring with a length direction parallel to the longitudinal axis of the stent. Similar spigots are envisaged in the present invention, preferably of reduced radial thickness relative to the radial thickness of the struts of the stenting ring. In such a case, each spigot could receive a seamless ring of radiopaque material, which could then be subject to a swaging procedure to plastically deform the radiopaque material while it is pressed and swaged onto the major surfaces of the spigot. The end result could be a ring of radiopaque marker "spoons" at first sight indistinguishable from the ring of marker spoons taught in WO2002/015820 each having opposed major surfaces, one convex and abluminal, the other concave and luminal, the abluminal surface being the "back" of the spoon. The absolute performance of the swaged spoons could fall short of that of the welded spoons of the WO document, because each spoon would have a core of somewhat less radiopaque material, namely, the nickel-titanium alloy of the stent itself. However, compensation for this loss of radiopacity could be achieved by using as the malleable material swaged around the nickel-titanium spigot a material such a gold that has a radiopacity higher than that of the tantalum proposed in WO2002/015820.

Readers will grasp that putting an electrically insulating coating on the carrier portions of the stent is a relatively straightforward procedure, readily accomplished, for example, in a furnace using an appropriately oxidising atmosphere. In any event, the rigorous measures that government regulatory agencies impose on stent manufacturers to minimise risk of fatigue failure has hitherto usually necessitated electrochemical processing of stent workpieces, in so-called "e-polishing" steps to eliminate the surface microcracks that can be the nucleators of fatigue cracks. One envisages elegantly combining the generation of the needed electrically insulated coating on the carrier portions with the surface polishing procedures that enhance performance in fatigue.

Readers will also grasp that electrochemical polishing procedures can introduce a degree of uncertainty in the absolute dimensions of the workpiece being polished. Such uncertainty of dimensions can be detrimental to quality control when it comes to procedures such as precision welding. However, a degree of uncertainty as to the absolute dimensions of a nickel-titanium spigot in a stent matrix could be tolerated when the procedure for turning the spigot into a radiopaque marker for the stent is a swaging procedure rather than a welding procedure. Any small variations of spigot dimensions would be subsumed within the plastic deformation of the relatively soft radiopaque marker material while it is being swaged onto the spigot. Thus, the present invention finds particular application in stent manufacturing regimes where electro-polishing is indicated, prior to equipping the stent matrix precursor with its radiopaque marker portions. This is likely to be a common situation, whenever the performance of the radiopaque marker material in electrochemical polishing is markedly different from that of the material of the stent matrix as such. If one were to schedule the electro-polishing procedure for a point in the manufacturing process downstream of assembly of marker portions to the stent matrix, it would be with the consequence that a degree of control would be lost, in the polishing step, because of the uncertainty of relative rates of dissolution of material, as between stent matrix material and radiopaque marker material. With the present invention, electro-polishing can be carried out with mono-metallic workpieces, rather than a bi-metallic workpiece.

Although an oxide layer is attractive as the layer of electrically insulating material between the stent metal and the marker metal, other possibilities will be evident to the skilled reader. For example, with relatively soft marker material such as relatively pure gold, pressing of the marker material onto the carrier portion of the stent matrix could be done without broaching an insulating layer of polymer interposed between the carrier portion and the radiopaque metal. Although a percussive procedure for plastic deformation of the radiopaque material is contemplated, that is, swaging, one can also envisage non-percussive pressing techniques. These would be preferable, one envisages, when the insulating layer relied upon is something relatively easily broached, such as a thin layer of polymer.

With pressing techniques, such as swaging and crimping, one has to take account of any tendency of the pressed material to recover elastically, that is to say, exhibit a spring-back tendency. In general, the softer the material, the less likely it will be to exhibit spring-back but, the harder the material, the more likely it is to remain pressed or crimped and to remain in position in the carrier portion. One envisages that the most secure attachment would come from a carrier portion that has non-planar surfaces to receive the pressed radiopaque material, such as apertured surfaces, even with re-entrant sidewall portions. Then, plastic deformation of soft radiopaque material, flowing it into the recesses, apertures or against the re-entrant wall portions, will enhance the degree of certainty that, during the time of residence of the stent in the body, there will be no relaxation and relative movement of the radiopaque material away from the carrier portion, even when the radiopaque material is very malleable.

For a better understanding of the present invention, and to show more clearly how the same may be carried into effect, reference will now be made, by way of example, to the accompanying drawings.

BRIEF DESCRIPTION OF THE DRAWINGS

FIG. 6b is a view of the sleeve comprising a radiopaque material shown in FIG. 6a.

In the Figures, like reference numerals denote like elements.

DETAILED DESCRIPTION

Figure 1:
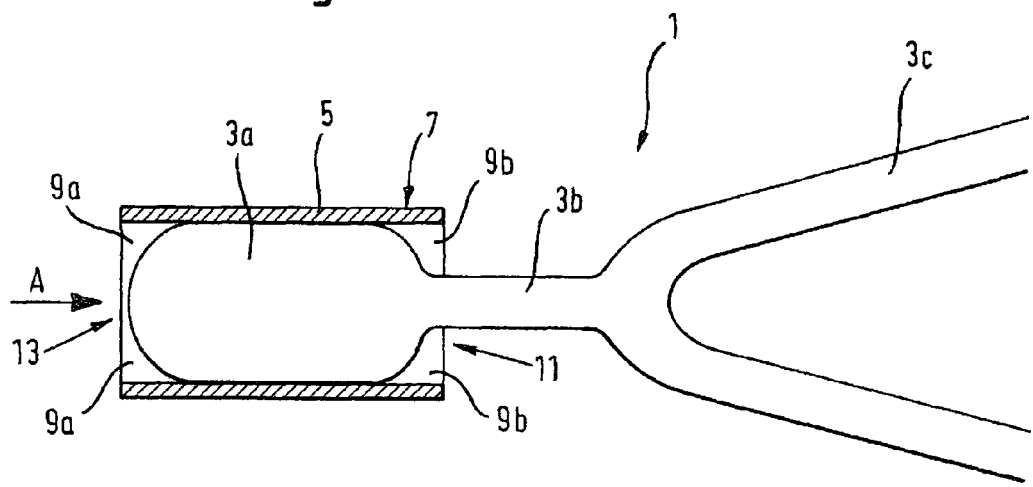
FIG. 1 is view from the side of a portion of a stent including a radiopaque marker prior to plastic deformation according to an embodiment of the invention.

FIG. 1 is view from the side of a portion of a stent including a radiopaque marker prior to plastic deformation according to an embodiment of the invention.

Figure 6A:
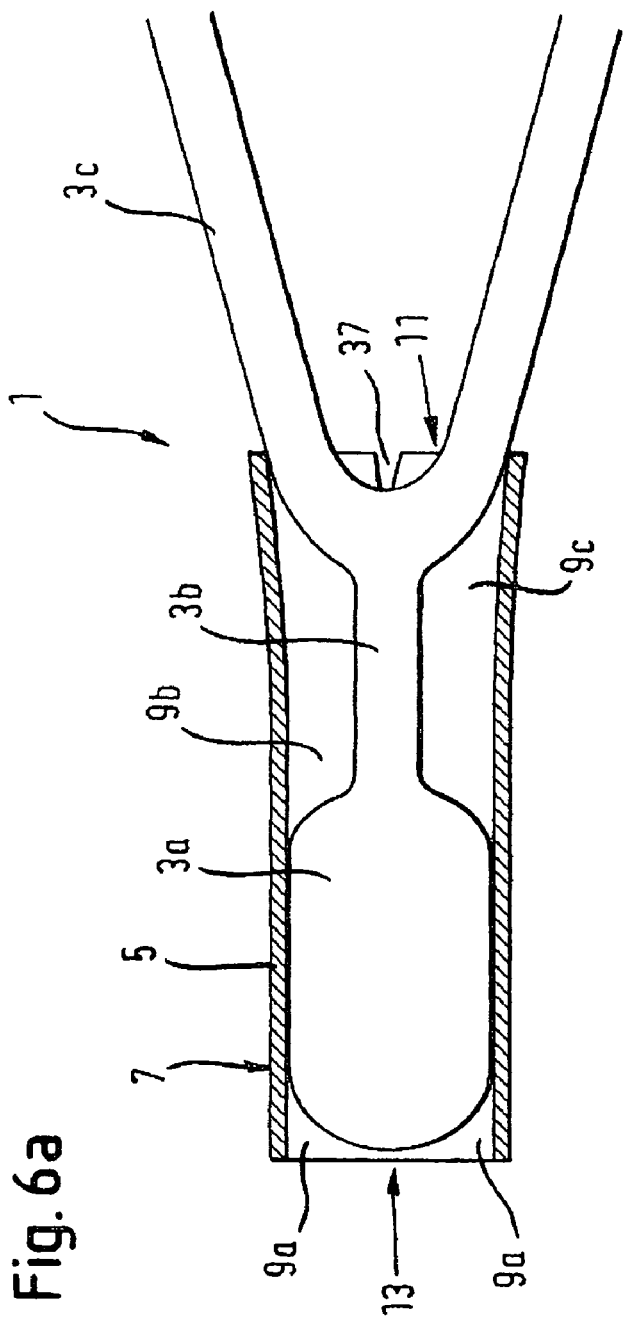
FIG. 6a is a side view of a stent including a radiopaque marker in the form of a sleeve prior to plastic deformation according to an embodiment of the invention.

FIG. 1 shows a portion of a stent 1 with radiopaque material 5 prior to plastic deformation. It has been found that by plastically deforming the radiopaque material 5 it may be secured to the stent 1. This avoids the need to have to weld the marker onto the stent 1. The stent 1 comprises a carrier portion 3a, 3b, 3c. The carrier portion 3a, 3b, 3c carries radiopaque material 5 which is provided on the stent 1. The carrier portion 3 may comprise a spigot 3a. It may further comprise an intermediate portion 3b and a shoulder portion 3c. Also shown with the stent 1 is radiopaque material 5. The radiopaque material 5 is provided on the stent 1. In the embodiment shown in FIG. 1 the radiopaque material is provided on the spigot 3a. However, in alternative embodiments, the radiopaque material may be provided on at least a portion of any one of the spigot 3a, intermediate portion 3b and the shoulder portion 3c, as shown in FIG. 6a. An embodiment of the invention includes sleeving the carrier portion 3a with the radiopaque material 5. The radiopaque material 5 may be provided in various forms. In one embodiment it is provided as a sleeve or seamless tube 7, as shown in FIGS. 1 and 6. In the embodiment shown in FIG. 1, the radiopaque material 5 is provided in the form of a seamless tube 7, and the carrier portion is a spigot 3a over which the tube 7 can be slipped. Once slipped onto the carrier portion 3, there is a tight fit between the carrier portion 3 and the tube 7. The internal diameter of the tube 7 is marginally greater than the external diameter of the carrier portion at its broadest point. In one embodiment, the tube 7 is a closed contour sleeve having a wall thickness of around 0.02 mm. In an alternative embodiment, the radiopaque material is provided as sheet material wrapped around the carrier portion 3a, 3b, 3c. In one embodiment, the sleeve comprises one or more overhanging portions 9a, 9b, 9c extending beyond at least one of a proximal and distal end 11, 13 of the carrier portion 3. The method may further include the step of folding the at least one or more overhanging portions 9a, 9b, 9c around the carrier portion 3.

Figure 2:
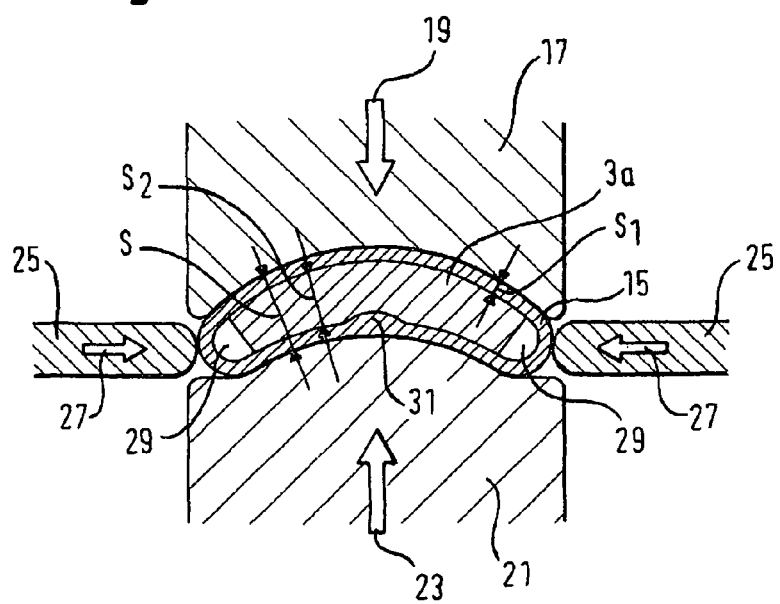
FIG. 2 is a cross section (view A) of the stent shown in FIG. 1 during plastic deformation of the radiopaque marker.

FIG. 2 is a cross section (view A) of the stent shown in FIG. 1 during plastic deformation of the radiopaque marker. The radiopaque material 5 is typically comprised in a marker on the stent 1. As discussed, the function of the marker is to enable a user to identify the stent when deployed in, for example, a body. The radiopaque material is plastically deformed as described hereinafter. The radiopaque material 5 may be taken from those known in the art. It has been found, that malleable materials with a high density are preferred, for example, gold, platinum.

Typically, the stent exhibits a generally annular form with luminal and abluminal major surfaces. Once formed, the marker 15 also exhibits opposed major luminal and abluminal surfaces. The marker 15 envelops the carrier portion 3a, 3b, 3c of the stent 1. The radiopaque material 5 may be plastically deformed by applying a radial press force to the sleeve using a contour press tool to radially deform the sleeve. In particular, the high density metal applied as a tube of sheet material is pressed into the surface of the carrier portion 3. This may be achieved using anvil tools as a contour press tool as shown in FIG. 2.

The anvil tools may comprise an upper anvil 17 which applies a pressing force in a downwards direction 19, a lower anvil 21 which applies a pressing force in an upwards direction and one or more side anvils 25 which apply a pressing force in a lateral direction 27. Prior to application of a pressing force, one or more spaces 29 may be defined between sleeve 7 or sheet material and the carrier portion 3. A press force may be applied via the contour press tool to radially deform (or thin) the radiopaque material 5. During pressing, the radiopaque material 5 is plastically deformed within the sleeve. In particular, the material flows to fill the one or more spaces 29 between the sleeve 7 and the carrier portion 3. In particular, it may flow tangentially to fill the one or more spaces 29 in the sleeve or sheet material. Further, the proximal and distal overhanging portions 9a, 9b are folded around the carrier portion 3, so as to conform with an outer surface of the carrier portion 3. FIG. 2 shows indented regions 31 that can receive plastically deformed radiopaque material and thereby achieve a mechanical interference fit or lock, between sleeve 7 and carrier portion 3 which stops the sleeve, after its plastic deformation, from sliding off the sleeve.

In one embodiment, the plastic deformation step is a swaging step.

In particular, the portions of the material of the resulting marker which exhibit evidence of plastic deformation secure the marker on the carrier portion by suppressing relative movement between the marker and the carrier portion. In this way, portions of the material of the marker which exhibit evidence of plastic deformation secure the marker on the carrier portion.

The thickness of the radiopaque material 5 and the pressing forces applied are selected to firstly cause the radiopaque to plastically deform. Reference being made to thickness dimensions S, $S_1$ and $S_2$ shown in FIG. 2:

1) S prior to forming is preferably slightly larger than S after forming (wherein S after forming is hereinafter referred to as S*; and
2) $S^* = 2S_1 + S_2$, where $S_1$ is equal to the thickness of the radiopaque material and $S_2$ is the thickness of the carrier portion 3.

Figure 3A:
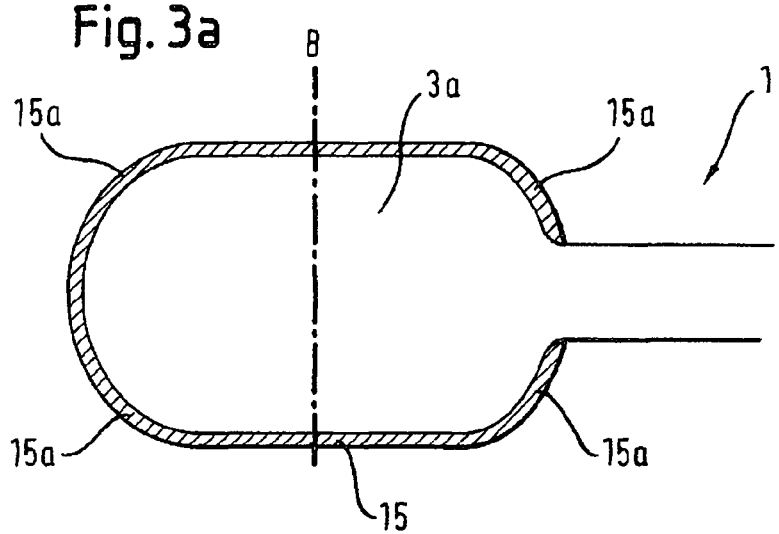
FIG. 3a is a side view of a portion of a stent with a radiopaque marker according to an embodiment of the invention.

FIG. 3a is a view of a portion of a stent with a radiopaque marker according to an embodiment of the invention, looking along a radius to the longitudinal axis of the stent. In particular, FIG. 3a shows a marker formed by the method shown and described with reference to FIG. 2. The resulting marker 15 comprises portions 15a that have been crimped around the carrier portion 3a. In general, it has been form-fitted to the contour of the carrier portion 3a. The marker 15 may extend over at least a portion of at least one of the spigot 3a, the intermediate portion and the shoulder portion. In the embodiment shown in FIG. 3a, the marker 15 extends over the spigot 3a. In an alternative embodiment shown in FIG. 6, the resulting marker extends over the spigot, the intermediate portion 3b and may further extend over the shoulder portion 3c.

Figure 3B:
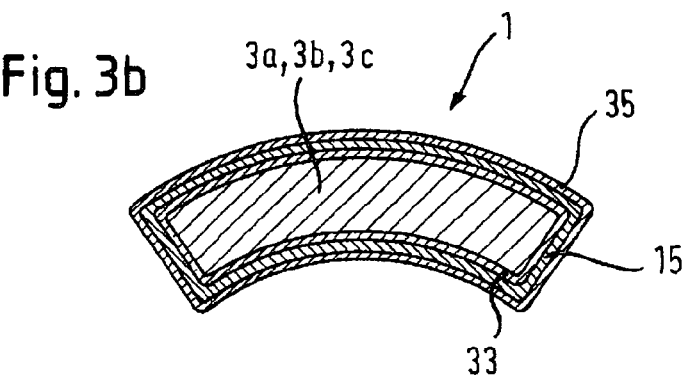
FIG. 3b is a cross section (view A) of stent with a radiopaque marker according to an embodiment of the invention.

FIG. 3b is a cross section (view A) of a carrier portion of a stent with a radiopaque marker according to an embodiment of the invention, viewed along a line parallel with the longitudinal axis of the stent. In further embodiments of the present invention an electrically insulating surface may be provided between the carrier portion 3a, 3b, 3c and the sleeve. In this way, after pressing, a layer of material 33 is provided between the marker 15 and the carrier portion 3a, 3b, 3c being more electrically insulating than the marker 15 or the material of the carrier portion which is substantially the same as the material of the stent. It has been found in a deployed stent, that the provision of an electrically insulating layer 33 between the marker 15 and the carrier portion 3a suppresses ion exchange in bodily fluids at a surface of at least one of the carrier portion 3 and the marker 15. In this way, it has been found that the metallic marker 15 may be added onto the carrier portion 3 without creating substantial intermetallic ion exchange zones. The electrically insulating material 33 may comprise a polymer material.

In a further embodiment, a protective coating 35 may overlie the sleeve. In this way, after pressing, a protective coating 35 is provided on the marker 15. The protective coating may be applied either to the sleeve 7 prior to pressing, or to the marker 15 after pressing. The protective coating 35 may comprise a polymer, such as fluorinated ethylene propylene (FEP). It has been found that coating the surface of the marker with a polymer coating suppresses any fluid which may act as a carrier from ions from entering between the marker and the carrier portion 3.

Figure 4:
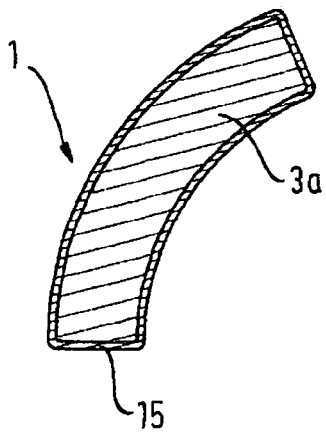
FIG. 4 is a cross section of the stent shown in FIG. 3a along line B.

FIG. 4 is a cross section of the stent shown in FIG. 3 along line B. In particular, FIG. 4 shows a carrier portion 3a on which a marker 15 is disposed. As mentioned above, in one embodiment, the carrier portion 3a may be provided with an electrically insulating material. The electrically insulating material may be provided in the form of a layer disposed around at least a portion of the carrier portion. In this way, the creation of substantial intermetallic ion exchange zones is suppressed. In the embodiment shown in FIG. 4 an electrically insulating material is not shown, but the absence of the showing of insulating material is purely for the sake of clarity. After all, it can be very thing indeed.

Figure 5:
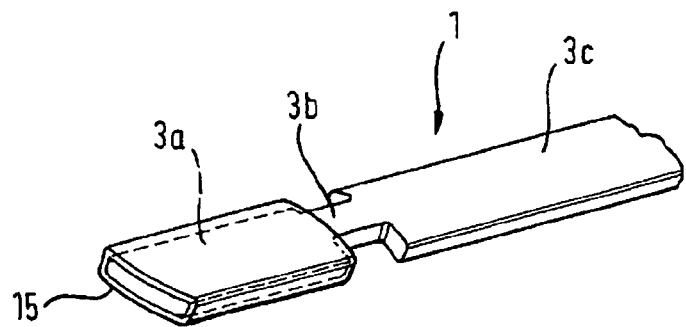
FIG. 5 is a view of a stent with a radiopaque marker according to an embodiment of the invention.
Figure 6B:
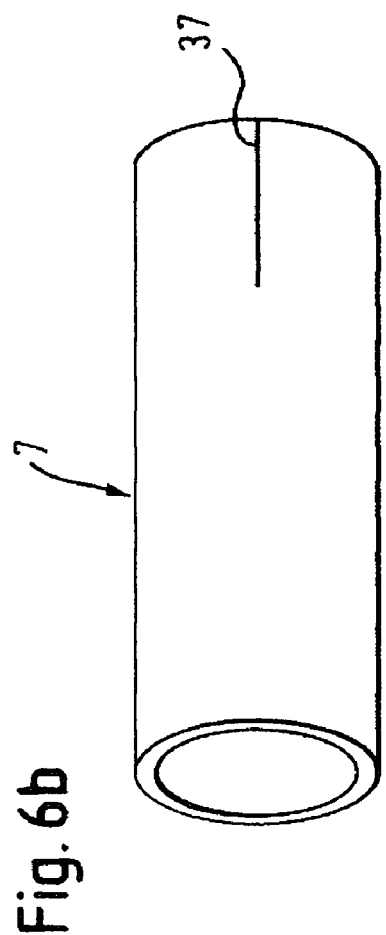

FIG. 5 is a view of a stent with a radiopaque marker according to an embodiment of the invention. In particular, FIG. 5 shows that the opposed major luminal and abluminal surfaces of the marker 15 once applied to the stent 1 extend in a radial direction beyond the opposed major luminal and abluminal surfaces of the stent. In an alternative embodiment (not shown), the dimensions of the stent, in particular, of the carrier portion 3a, 3b, 3c are configured so that the opposed major luminal and abluminal surfaces of the marker 15 once applied to the stent 1 are flush with the luminal and abluminal major surfaces of the stent. In this way, the marker 15 can be applied to the stent without affecting the manner in which the spoons cooperate in the delivery configuration. Further, in the deployed configuration, the stent maintains a smooth outer surface. FIG. 6a is a side view of a stent including a radiopaque marker in the form of a sleeve prior to plastic deformation according to an embodiment of the invention. FIG. 6b is a view of the sleeve comprising a radiopaque material shown in FIG. 6a. In one embodiment, the marker 15 may extend beyond the spigot. It may extend further along the stent along at least a portion of the intermediate portion 3b and the shoulder portion 3c. In this way, the radiopacity is improved not only on the stent ends but also along the stent. The radiopaque material 5 in such embodiments may be pressed in the manner described above. In an alternative embodiment, the marker 15 may be applied to a portion of the intermediate portion 3b or the shoulder portion 3c, not necessarily to the spigot. In certain embodiments, for example, where the radiopaque material is provided in the form of a seamless tube, the tube may further be provided with a slit 37. In this way, the tube is provided with more flexibility. Further, in this way, it may be more readily slipped over broader portions of the stent, for example, the shoulder portion 3c. As mentioned, the sleeve 7 shown in FIGS. 6a and 6b may be formed in the same manner as described with reference to FIG. 2. Such a sleeve in addition to overhanging portions 9a and 9b, may also include an intermediate overhanging portion 9c. The intermediate overhanging portion 9c may be folded around the intermediate portion 3b. This may be achieved, for example, by pressing forces applied by the anvil tools described above.

The scope of protection of the claims which follow is not to be limited to the embodiments described in detail above. Readers will appreciate that the detailed description is to assist in realising embodiment within the scope of the claim rather than to set a limit on the scope of protection.

The invention claimed is:

1. A stent with a radiopaque marker, the stent exhibiting a generally annular form with luminal and abluminal major surfaces, the marker also exhibiting opposed major luminal and abluminal surfaces, wherein:
   i) the marker envelops a carrier portion of the stent;
   ii) the marker comprises a sleeve comprising:
   a lumen connecting a proximal opening to a distal opening; and
   one or more overhanging portions extending beyond at least one of a proximal and distal end of the carrier portion, the one or more overhanging portions being folded around the carrier portion;
   iii) separating the marker and the carrier portion is an electrically insulating surface; and
   iv) portions of the material of the marker which exhibit evidence of plastic deformation secure the marker on the carrier portion.

2. The stent with a radiopaque marker according to claim 1, wherein the portions of the material of the marker which exhibit evidence of plastic deformation secure the marker on the carrier portion by suppressing relative movement between the marker and the carrier portion.

3. The stent with a radiopaque marker according to claim 1, further comprising a layer of material provided between the marker and the carrier portion, the layer of material being more electrically insulating than the marker or the stem.

4. The stent with a radiopaque marker according to claim 1, further comprising a protective coating on the marker, such as fluorinated ethylene propylene (FEP).

5. The stent with a radiopaque marker according to claim 1, wherein the marker exhibits opposed major luminal and abluminal surfaces that are each portions of a cylindrical surface with its axis co-incident with that of the stent.

6. The stent with a radiopaque marker according to claim 1, wherein the carrier portion has a radial thickness which is less than that of other portions of the stent.

7. The stent with a radiopaque marker according to claim 1, wherein the material within the sleeve is deformed so a space between the marker and the carrier portion prior to plastic deformation is filled with material after plastic deformation.

8. The stent with a radiopaque marker according to claim 1, wherein the carrier portion comprises a spigot portion, an intermediate portion, and/or a shoulder portion, and wherein the marker extends over at least a portion of at least one of the spigot portion, the intermediate portion, and the shoulder portion.

9. The stent with a radiopaque marker according to claim 1, wherein the radiopaque material is provided in the form of a seamless tube, wherein the tube is provided with a slit.

10. The stent with a radiopaque marker according to claim 1, wherein the opposed major luminal and abluminal surfaces of the marker once applied to the stent extend in a radial direction beyond the opposed major luminal and abluminal surfaces of the stent.

11. A device for placing in the body, comprising:
   a stent exhibiting a generally annular form having a luminal major surface and an abluminal major surface, the stent including a carrier portion;
   a radiopaque marker comprising a sleeve having a lumen connecting a proximal opening to a distal opening, the sleeve including one or more overhanging portions folded around at least one of a proximal end and a distal end of the carrier portion, the radiopaque marker enveloping the carrier portion, wherein portions of the sleeve exhibiting evidence of plastic deformation secure the marker on the carrier portion; and
   an electrically insulating surface separating the radiopaque marker and the carrier portion.

12. The device according to claim 11, further comprising a protective coating on the marker, such as fluorinated ethylene propylene (FEP).

13. The device according to claim 11, wherein the carrier portion has a radial thickness which is less than that of other portions of the stent.

14. The device according to claim 11, wherein the radiopaque material is provided in the form of a seamless tube, wherein the tube is provided with a slit.

* * * * *